United States Patent [19]

Junino et al.

[11] Patent Number: 5,244,497

[45] Date of Patent: Sep. 14, 1993

[54] PROCESS FOR THE PREPARATION OF A MELANIC PIGMENT BY AN ENZYME ROUTE AND ITS USE IN COSMETICS

[75] Inventors: Alex Junino, Livry-Gargan; Herve Andrean, Paris; Remi Tuloup, Miniac-sous-Bécherel, all of France; Irwing J. Higgins, Bedford, England

[73] Assignee: L'Oreal, Paris, France

[21] Appl. No.: 649,865

[22] Filed: Feb. 5, 1991

[30] Foreign Application Priority Data

Feb. 5, 1990 [LU] Luxembourg .......................... 87672

[51] Int. Cl.⁵ .............................................. A61K 7/021
[52] U.S. Cl. ..................................... 106/498; 424/62; 424/63; 424/401; 106/493; 8/423
[58] Field of Search ................. 424/401, 62, 63; 106/493, 498; 8/423

[56] References Cited

U.S. PATENT DOCUMENTS

| | | | |
|---|---|---|---|
| 4,776,857 | 10/1988 | Carroll et al. | 8/423 |
| 4,804,385 | 2/1989 | Grollier et al. | 8/423 |
| 4,822,375 | 4/1989 | Lang et al. | 8/423 |
| 4,888,027 | 12/1989 | Grollier et al. | 8/423 |
| 4,961,754 | 10/1990 | Grollier et al. | 424/69 |
| 5,011,500 | 4/1991 | Grollier et al. | 8/423 |
| 5,021,067 | 6/1991 | Grollier | 8/423 |
| 5,034,015 | 7/1991 | Junino et al. | 8/423 |
| 5,073,174 | 12/1991 | Vayssie et al. | 8/423 |

FOREIGN PATENT DOCUMENTS 2207153 1/1989 United Kingdom .

OTHER PUBLICATIONS

Tetrahedron, vol. 44, No. 23, 1988, pp. 7265–7270, Napolitano et al: "A profile of the oxidation chemistry of 5-hydroxyindole under biomimetic conditions".
Chemical Abstracts, vol. 78, No. 16, Apr. 1973, No. 98091p, Fattorusso et al: "Polymerization process of 5,6 dihydroxyindole".
European Search Report of Luxembourg 87 672.

Primary Examiner—Thurman K. Page
Assistant Examiner—Amy Hulina
Attorney, Agent, or Firm—Cushman, Darby & Cushman

[57] ABSTRACT

The invention relates to a process for the preparation of a melanic pigment, comprising the polymerisation of a compound corresponding to the formula:

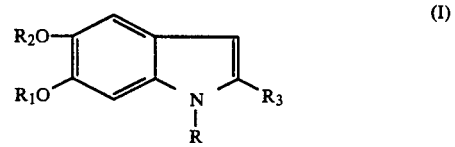

(I)

in which:

R denotes a hydrogen atom, an alkyl, alkoxy, hydroxyalkyl, $SiR_4R_5R_6$ or aminoalkyl radical, or an aryl radical which is unsubstituted or substituted by OH, $NH_2$, alkyl, alkoxy or $NO_2$;

$R_1$ and $R_2$ denote alkyl groups or together form a methylene or ethylene group which is optionally substituted by one or more alkyl groups, and $R_2$ denotes hydrogen or COOH, in the presence of an oxidizing medium and of an enzyme with (per)oxidizing activity or of a compound which has a similar activity, and to powders which make use of them and to their cosmetic use.

12 Claims, No Drawings

PROCESS FOR THE PREPARATION OF A MELANIC PIGMENT BY AN ENZYME ROUTE AND ITS USE IN COSMETICS

The invention relates to a new process for the preparation of melanic pigments by an enzyme route, and to their use, especially in cosmetics.

The use of colored pigments is of very great interest in the cosmetic field.

It involves essentially inorganic pigments or pigments originating from synthetic direct colorants, or from pure carbon in the case of black pigments.

These various products can present problems in use, and some of them are not completely harmless.

It is known that yellow-brown colorants can be produced by oxidizing 5-hydroxyindole with horseradish peroxidase in the presence of aqueous hydrogen peroxide. This colorant consists of 5-hydroxyindole dimers and trimers (A. Napolitano et al., Tetrahedron, Vol. 44, No. 23, pages 7265-7270—1988).

It is also known that 9-methoxyellipticine can be demethylated with horseradish peroxidase in the presence of aqueous hydrogen peroxide to form chiefly 9-oxo-ellipticine (Gerard Meunier et al., J. Am. Chem. Soc., 1985, 107, 2558-2560). This process enables the quinone imine to be obtained in yields of at least 90%.

The Applicants have surprisingly found that melanic pigments can be prepared by an enzyme route, by oxidative polymerization of 5,6-dihydroxyindole derivatives in which the hydroxyl functional groups are blocked. These 5,6-dihydroxyindole derivatives have the advantage of being stable and relatively low in cost.

The pigment obtained by this process is easier to incorporate into cosmetic compositions because of its ease of dispersion and its small particle size.

The subject of the invention consists, therefore, of a process for the preparation of a melanic pigment and the pigment thus obtained.

The name "melanic pigment" is given to the pigment resulting from the oxidative polymerization of precursors related to indole; this pigment is identical with, or similar to, melanin.

Other subjects of the invention will become apparent on reading the description and the examples which follow.

The process for the preparation of the melanic pigment is essentially characterised in that a compound is polymerized which corresponds to the formula:

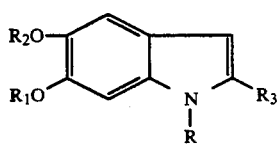

(I)

in which:

R denotes a hydrogen atom or an alkyl, alkoxy, hydroxyalkyl, aminoalkyl or $SiR_4R_5R_6$ radical, where $R_4$, $R_5$ and $R_6$ denote an alkyl group, in which the alkyl residue contains from 1 to 8 carbon atoms, or an aryl radical which is unsubstituted or substituted by OH, $NH_2$, alkyl, alkoxy or $NO_2$;

$R_1$ and $R_2$, which are identical or different, denote alkyl groups or together form a methylene or ethylene group which is optionally substituted by one or more alkyl groups, and $R_2$ denotes a hydrogen atom or the COOH radical, in the presence of an oxidizing medium and of an enzyme with (per)oxidizing activity or of a compound which has a similar activity.

The alkyl or alkoxy radicals preferably denote lower radicals containing 1 to 6 carbon atoms; aryl preferably denotes phenyl.

The compounds corresponding to the formula (I) shown above are preferably chosen from 5,6-dimethoxyindole, 5,6-methylenedioxyindole and 1-methyl 5,6-dimethoxyindole.

The oxidizing medium may consist of peroxides such as hydrogen peroxide or persalts such as potassium monopersulphate (oxone), or of atmospheric oxygen, depending on the nature of the enzymes with oxidizing activity which are used.

These enzymes, with peroxidizing activity, are chosen from horseradish peroxidase, chloroperoxidase, milk peroxidase, cytochrome C peroxidase and microperoxidase.

The compounds which have an activity similar to that of the enzymes with peroxidizing activity are chosen from crude or purified haemoglobin, myoglobin, methaemoglobin and metmyoglobin.

The enzymes with oxidizing activity are chosen from alcohol-oxidases such as methanol-oxidase, polyphenol-oxidases, or dealkylating monooxygenases such as the enzymes produced by the microorganism Pseudomonas testosteroni. D. W. Ribbons, FEBS Letters, 8 (1970), p.101).

Horseradish peroxidase, haemoglobin and methaemoglobin are particularly preferred.

In the case of haemoglobin, potassium ferricyanide may be added to the reaction mixture to convert it into methaemoglobin.

When haemoglobin, myoglobin, methaemoglobin or metmyoglobin is employed, an inorganic salt like ammonium sulphate or an organic product such as formamide or guanidine in the form of hydrochloride may be added to the reaction mixture.

The concentration of hydrogen peroxide employed with the enzymes with peroxidizing activity is low and generally lower than 5% by weight relative to the total weight of the reaction mixture and preferably lower than 2%, the minimum concentration being 0.007%.

The concentration of persalt is between 2 and 600 millimoles/liter.

In the case of methanol-oxidase, this is employed in the presence of methanol or ethanol and atmospheric oxygen as oxidising agent.

The weight relationship between the indole-related derivative of formula (I) and the enzyme with oxidizing activity or the compound which has a similar activity may vary in wide proportions ranging from 1 to $10^6$.

The preparation of the melanic pigment is generally performed at a pH which is compatible with the enzymes used and is generally between 2 and 11, and preferably between 4 and 8. This pH is obtained with the aid of a buffer which is appropriate to the enzyme in question, such as, for example, an acetate buffer, a phosphate buffer or a citrate buffer.

The reaction temperature is compatible with the enzymes employed and is generally between 10° C. and 50° C. and preferably between 20° and 45° C.

The reaction medium generally consists of water or a mixture of water and organic solvent. In some cases this medium may consist solely of an organic solvent when hydroperoxides other than hydrogen peroxide are employed.

The solvents which may be employed are chosen especially from aromatic hydrocarbons such as toluene, or esters such as ethyl acetate, or dimethylformamide, N-methylpyrrolidone, dimethyl sulphoxide, dioxane and acetone.

The formation of the melanic pigment must be performed in conditions which are such as to have a good dispersion of the enzyme in the reaction mixture. It may thus be performed by immobilizing the enzyme on the surface of a suitable support, or else a chemically modified enzyme may be employed so as to facilitate its solubilization in the reaction mixture.

A preferred embodiment consists in immobilizing horseradish peroxidase by the technique of drying the enzyme with air on the surface of glass beads, as described in the Journal of American Chemical Society, 107, 5448, by R. Z. Kazantjian and Klibanov, 1985.

In a preferred embodiment an enzyme with peroxidizing activity is added to a solution of indole-related precursor of formula (I) in an aqueous solvent medium and, after 1 to 30 minutes, a solution of hydrogen peroxide is added. After 1 to 24 hours a brown-to-black precipitate is separated off by filtration, centrifuging or freeze-drying. This precipitate is optionally washed with water or with an organic solvent such as those mentioned above and is then dried.

The pigments according to the invention may be characterized by EPR (electron paramagnetic resonance) with the aid of a Brucker ER 200 D spectrometer at 9.52 GHz with a field modulation frequency of 100 kHz and a microwave power of 1.9 mW. The absorption of this wave by the pigment as a function of the field is recorded and a maximum absorption is found at about 3480 gauss. This absorption maximum is also found in natural eumelanins.

The melanic pigment thus prepared can be employed in diverse applications where it is desired to have available a brown-to-black pigment, such as especially in cosmetics in make-up products, sun compositions and hair-coloring products.

With a view to these applications they may be introduced into a cosmetically acceptable medium based on water or on mixtures of water and organic solvent(s) or on one or more solvents, and optionally other additives usually employed in cosmetics, such as surface-active agents, thickeners, stabilizers, etc.

According to an alternative form of the invention, the melanic pigment may be deposited onto an inorganic filler consisting of inert particles which have a particle size smaller than 20 microns and preferably 10 microns. The pigment may also be deposited and/or absorbed onto an organic filler consisting of polymer particles which have a particle size smaller than 100 microns or onto a crosslinked polymeric material forming microspheres, as described in application EP 313,380.

According to another alternative form the pigment may be deposited and/or absorbed onto organic or inorganic particles with a lamellar structure smaller than 50 microns by the largest dimension.

A powder whose color shades range from brown to black is thus obtained, and can be employed in cosmetics.

According to this alternative form this colored powder may be prepared by dispersing the inorganic or organic particles in the solution of indole-related precursor of formula (I) containing the enzyme. The conditions of oxidation of the precursor of formula (I) are identical with those described above and, especially in the case where an enzyme or a compound with activity similar to peroxidizing activity is employed, the solution additionally contains hydrogen peroxide or a persalt.

After 1 minute to 24 hours of reaction, the powder containing the pigment is separated off by filtration, is washed with water or with an organic solvent and is dried.

This powder can also be prepared by absorbing the melanic pigment prepared in accordance with the invention onto and into the inorganic or organic particles defined above.

The procedure, in particular, is to disperse the melanic pigment formed beforehand in a medium which is a nonsolvent for the particles and contains the said particles, and after pigment absorption these are dried.

More particularly, particles of calcium carbonate or of silica which have a particle size generally greater than 0.01 micron are employed as the inorganic filler.

The organic filler employed is preferably particles of polymers derived from optionally modified keratin, of polymers derived from optionally deacetylated chitin, of silk fibroin, of synthetic polymers chosen from crosslinked polymethyl methacrylate, crosslinked poly-$\beta$-alanine, hollow microspheres of vinylidene chloride/acrylonitrile copolymer or porous microspheres of polyamide 12, polyamide 6 or copolyamide 6/12, of silicone powders consisting of gums, resins or organopolysiloxane elastomers.

These particles have a particle size which is preferably greater than 0.01 micron.

As the crosslinked polymeric material there may be mentioned microspheres of styrene/divinylbenzene or methyl methacrylate/ethylene glycol dimethacrylate, whose particle size is preferably between 5 and 100 microns.

The organic or inorganic particles with lamellar structure which are employed are preferably L-lauroyllysine, ceramic microparticles optionally coated with zirconium powder, lamellar titanium dioxide, lamellar talc, boron nitrite, mica and bismuth oxychloride. These particles have a particle size which is preferably larger than 0.5 micron and smaller than 50 microns, the relationship between the largest dimension and the thickness being between 2 and 100.

The examples which follow are intended to illustrate the invention without, however, being limiting in nature.

EXAMPLE OF PREPARATION 1

Preparation of a melanic pigment from 5,6-dimethoxyindole 0.378 g of horseradish peroxidase (Sigma) and 1 g of 5,6-dimethoxyindole in 8 ml of DMF are added to 4 liters of a sodium acetate buffer (20 nMoles-pH 5).

15 minutes after the addition of the enzyme, 8 ml of 110-volume aqueous hydrogen peroxide are added.

The reaction mixture is left stirred for 6 hours and then left to stand overnight at room temperature. After centrifuging followed by washing with water, the black pigment is dried under vacuum.

EPR analysis shows a maximum absorption at about 3480 gauss.

EXAMPLE OF PREPARATION 2

Preparation of a melanic pigment from 5,6-methylenedioxyindole.

0.6 g of horseradish peroxidase (Sigma) and 1.6 g of 5,6-methylenedioxyindole in 13 ml of dimethylformamide are added to 6.4 l of a sodium acetate buffer (20 nMoles-pH 5).

15 minutes after the addition of the enzyme, 12.8 ml of 110-volume aqueous hydrogen peroxide are added.

The reaction mixture is left at room temperature for 36 hours. After centrifuging followed by washing with water, the black pigment obtained is dried under vacuum.

EPR analysis shows a maximum absorption at about 3480 gauss.

EXAMPLE OF PREPARATION 3

Preparation of a melanic pigment from 5,6-dimethoxyindole.

After dissolving at room temperature, with stirring, 1 g of commercial haemoglobin sold by Sigma in 50 cm$^3$ of 0.1M sodium citrate-citric acid buffer solution, adjusted to pH=5.5, 30 g of ammonium sulphate are added. After stirring for ½ an hour, the solution is centrifuged for 20 minutes at 10,000 revolutions/minute. The haemoglobin deposited is taken up with 500 cm$^3$ of 0.1M sodium acetate-acetic acid buffer solution, adjusted to pH=5 and brought to a temperature of 37° C. 60 mg of potassium ferricyanide are added to the solution, followed ½ an hour later by 1 g of 5,6-dimethoxyindole dissolved in 4 cm$^3$ of dimethylformamide. 4 cm$^3$ of 110-volume aqueous hydrogen peroxide are then poured in with vigorous stirring.

The reaction mixture is left stirred at 37° C. for 4 hours and is then centrifuged. The pigment is greenish in color. The black pigment is obtained by washing with dimethylformamide, with acetone and then with water, and is dried under vacuum.

EPR analysis shows a maximum absorption at about 3480 gauss.

EXAMPLE OF PREPARATION 4

Preparation of a melanic pigment from 5,6-dimethoxyindole.

1 g of commercial haemoglobin sold by Sigma is dissolved with stirring in 100 cm$^3$ of distilled water at room temperature. After dissolving, 1 g of 5,6-dimethoxyindole in 4 cm$^3$ of dimethylformamide is poured in, followed by 3.4 g of oxone (potassium monopersulphate triple salt) powder. The reaction mixture is left for 5 minutes at room temperature with stirring and is then centrifuged. The pigment is greenish in color. The black pigment is obtained by washing with dimethylformamide, with acetone and then with water, and is dried under vacuum.

EPR analysis shows a maximum absorption at about

EXAMPLE OF PREPARATION 5

Preparation of a melanic pigment from 5,6-dimethoxyindole.

1 g of commercial haemoglobin sold by Sigma is dissolved in 500 cm$^3$ of sodium acetate-acetic acid buffer, adjusted to pH=5 and containing 0.1 g of formamide (or 0.1 g of guanidinium hydrochloride). After stirring for 1 hour at 37° C., 1 g of 5,6-dimethoxyindole in 4 cm$^3$ of DMF is added, followed by 4 cm$^3$ of 110-volume aqueous hydrogen peroxide. The reaction mixture is left stirred at 37° for 4 hours and is then centrifuged. The black pigment obtained is washed with DMF, with acetone and then with water and is dried under vacuum.

EPR analysis shows a maximum absorption at about 3480 gauss.

EXAMPLE OF PREPARATION 6

Preparation of a melanic pigment from 5,6-dimethoxyindole.

1 g of commercial haemoglobin sold by Sigma is dissolved in 500 cm$^3$ of sodium acetate-acetic acid buffer, adjusted to pH=5.1 g of 5,6-dimethoxyindole in 4 cm$^3$ of DMF is added, followed by 4 cm$^3$ of 110-volume aqueous hydrogen peroxide. The reaction mixture is left stirred at 37° C. for 4 hours and is then centrifuged. The brown pigment obtained is washed with DMF, with acetone and then with water, and is dried under vacuum.

EPR analysis shows a maximum absorption at about 3480 gauss.

EXAMPLE OF PREPARATION 7

Preparation of a melanic pigment from 1-methyl-5,6-dimethoxyindole.

After dissolving at room temperature, with stirring, 1 g of commercial haemoglobin sold by Sigma in 50 cm$^3$ of 0.1M sodium citrate-citric acid buffer solution, adjusted to pH=5.5, 30 g of ammonium sulphate are added. After stirring for ½ an hour, the solution is centrifuged for 20 minutes at 10,000 revolutions/minute. The haemoglobin deposited is taken up with 500 cm$^3$ of 0.1M sodium acetate-acetic acid buffer solution, adjusted to pH=5 and brought to a temperature of 37° C. 60 mg of potassium ferricyanide are added to the solution. The mixture is left for ½ an hour with vigorous stirring and then 1 g of 1-methyl-5,6-dimethoxyindole dissolved in 4 cm$^3$ of DMF is added to it, followed by 4 cm$^3$ of 110-volume aqueous hydrogen peroxide.

The reaction mixture is left stirred at 37° C. for 4 hours and is then centrifuged. The brown pigment obtained is washed with DMF, with acetone and then with water, and is dried under vacuum.

EPR analysis shows a maximum absorption at about 3480 gauss.

EXAMPLE OF APPLICATION

| EXAMPLE A: MASCARA CREAM | |
| --- | --- |
| Black pigment obtained according to Example 1 | 15.0 g |
| Triethanolamine stearate | 15.0 g |
| Candelilla wax | 8.0 g |
| Carnauba wax | 10.0 g |
| Hydroxyethyl cellulose | 0.9 g |
| Keratin hydrolyzate (expressed as dry substance) | 0.75 g |
| Stabilizers q.s. | |
| Water q.s. | 100.0 g |

The pigment obtained in Example 3 may be employed instead of that obtained in Example 1.

| EXAMPLE B: HAIR GEL | |
| --- | --- |
| Black pigment obtained according to Example 2 | 0.5 g |
| Vinylpyrrolidone/vinyl acetate copolymer sold under the name PVP/VA S 630 by GAP | 1.5 g |
| Ethyl alcohol | 15.0 g |

| | |
|---|---|
| Carbopol 940 (Goodrich Chemical) | 0.7 g |
| Triethanolamine q.s. | pH = 7.5 |
| Stabilizers q.s. | |
| Water q.s. | 100.0 g |

The pigment obtained in Example 5 may be employed instead of that obtained in Example 2.

The pigment obtained in Example 5 may be employed instead of that obtained in Example 2.

We claim:

1. A process for the preparation of a melanic pigment comprising polymerizing in a polymerization medium a compound having the formula

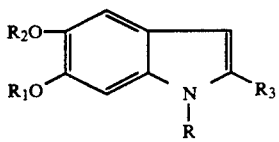

(I)

wherein

R represents hydrogen, alkyl, alkoxy, hydroxyalkyl, aminoalkyl or $SiR_4R_5R_6$ wherein $R_4$, $R_5$ and $R_6$ represent alkyl containing 1-8 carbon atoms or aryl unsubstituted or substituted by OH, $NH_2$, alkyl, alkoxy or $NO_2$, $R_1$ and $R_2$, each independently, represent lower alkyl, or $R_1$ and $R_2$ taken together form a methylene or ethylene group optionally substituted by one or more lower alkyl groups, and $R_3$ represents hydrogen or COOH, said polymerization medium comprising (i) hydrogen peroxide or oxone as an oxidizing medium and (ii) horseradish peroxidase as an enzyme having (per) oxidizing activity or haemoglobin as a compound having a (per) oxidizing activity.

2. A process for the preparation of a melanic pigment comprising polymerizing in a polymerization medium a compound having the formula

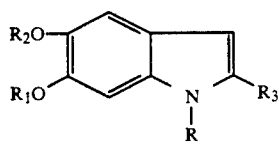

(I)

wherein

R represents hydrogen, alkyl, alkoxy, hydroxyalkyl, aminoalkyl or $SiR_4R_5R_6$ wherein $R_4$, $R_5$ and $R_6$ represent alkyl containing 1-8 carbon atoms or aryl unsubstituted or substituted by OH, $NH_2$, alkyl, alkoxy or $NO_2$, $R_1$ and $R_2$, each independently, represent lower alkyl, or $R_1$ and $R_2$ taken together form a methylene or ethylene group optionally substituted by one or more lower alkyl groups, and $R_3$ represents hydrogen or COOH, said polymerization medium comprising (i) an oxidizing medium and (ii) at least one of (1) an enzyme having (per)oxidizing activity and selected from the group consisting of horseradish peroxidase, chloroperoxidase, milk peroxidase, cytochrome C peroxidase and microperoxidase, (2) a compound having (per)oxidizing activity and selected from the group consisting of haemoglobin, myoglobin, methaemoglobin and metmyoglobin and (3) an enzyme having oxidizing activity and selected from the group consisting of an alcoholoxidase, a polyphenol-oxidase and a dealkylating monooxygenase.

3. The process of claim 2 wherein the weight relationship between said compound of formula (I) and said enzyme having (per)oxidizing activity or a compound having (per)oxidizing activity or an enzyme having oxidizing activity is between 1 and $10^6$.

4. The process of claim 1 wherein said compound of formula (I) is selected from the group consisting of 5,6-dimethoxyindole, 5,6-methylenedioxyindole and 1-methyl 5,6-dimethoxyindole.

5. The process of claim 2 wherein said oxidizing medium contains hydrogen peroxide or a persalt.

6. The process of claim 2 wherein said alcohol-oxidase is a methanol-oxidase.

7. The process of claim 2 wherein said polymerization medium also contains a reaction medium consisting of water or a mixture of water and an organic solvent and the concentration of hydrogen peroxide in said polymerization medium is lower than 5 percent by weight relative to the total weight of said reaction medium.

8. The process of claim 7 which includes maintaining the pH of said reaction medium at a value ranging from 2 to 11 using a buffer appropriate to the enzyme employed.

9. The process of claim 1 wherein the polymerization temperature ranges from 10° to 50° C.

10. The process of claim 1 wherein the polymerization temperature ranges from 20° to 45° C.

11. The process of claim 1 which includes immobilizing said enzyme on the surface of a support.

12. A melanic pigment made in accordance with the process of claim 1.

* * * * *